United States Patent [19]
Franz et al.

[11] Patent Number: 5,830,123
[45] Date of Patent: Nov. 3, 1998

[54] PIVOTABLE IRRADIATING DEVICE

[75] Inventors: Wolfgang Franz, Lübeck; Helmut Holtmann, Stockelsdorf, both of Germany

[73] Assignee: Drägerwerk AG, Lubeck, Germany

[21] Appl. No.: 709,481

[22] Filed: Sep. 6, 1996

[30] Foreign Application Priority Data

Sep. 9, 1995 [DE] Germany ................. 195 33 391.8

[51] Int. Cl.⁶ ................................................. A61B 11/00
[52] U.S. Cl. ................................. 600/22; 607/91; 607/96
[58] Field of Search ...................... 607/88–91, 94–96, 607/100, 101, 112; 606/1, 2, 27, 33, 34, 130; 600/21, 22, 473, 476

[56] References Cited

U.S. PATENT DOCUMENTS 1,429,443  9/1922  McFaddin ................................ 607/90
4,809,677  3/1989  Mackin et al. .......................... 600/22

FOREIGN PATENT DOCUMENTS 3528282  2/1986  Germany .................................. 607/88

*Primary Examiner*—John P. Lacyk
*Assistant Examiner*—Rosiland Kearney
*Attorney, Agent, or Firm*—McGlew and Tuttle

[57] ABSTRACT

A pivotable irradiating device for a person on a lying surface provides extensively uniform continued irradiation of the lying surface without any interruption in time when the irradiating device is pivoted out of the starting position. The irradiating device has at least one radiator in a housing. The housing is connected to a securing element via a rotatable connector (hinge). The axis of rotation of the hinge is located outside a central axis of the irradiating device. The intersection of these two axes is located in the center of the lying surface or in its vicinity.

18 Claims, 3 Drawing Sheets

PIVOTABLE IRRADIATING DEVICE

FIELD OF THE INVENTION

The present invention pertains to a pivotable irradiating device, and in particular to a pivotable irradiating device for supplying heat to a person or patient lying on a support surface.

BACKGROUND OF THE INVENTION

Irradiating devices of this type are used to keep premature babies, infants or toddlers warm, who lie on a lying surface accessible from a plurality of sides and must be cared for and treated by the nursing personnel possibly without hindrance. The use of infrared radiators, sometimes combined with suitable light radiators for phototherapy and illumination, for keeping patients warm has been known.

An irradiating device with infrared radiator for supplying a person on a lying surface with heat was described in Utility Model No. DE-76 02 145.9.

A pivotable irradiating device equipped preferably with solarium lamps, with which a housing containing irradiation tubes can be brought into a desired position for irradiating a person via two hinges, has been known from Utility Model No. DE-78 14 168.

In the case of premature and newborn babies, it is necessary to ensure uniform irradiation of the lying support surface to the greatest extent possible without interruption in time and without any essential fluctuation in the radiation output received by the patient.

As a quality/efficiency criterion for the uniform irradiation of the lying support surface, it is desirable for the center of the lines of equal energy density and the center of the lying surface to coincide in the ideal case. The energy density distribution in the area of the lying surface and thus the distribution for the patient shall be as uniform as possible, and the highest possible percentage of the radiation shall reach the lying surface. Elliptical, concentric lines of equal energy density are usually obtained in practice on the lying surface.

If the patients must be X-rayed, the X-ray apparatus with the emission head is placed approximately above the center of the lying surface. Since the irradiating device for supplying heat is normally located there, it must be removed for the X-ray procedure, including the preparation and assessment time. However, it is very important for the heat radiation to continue to warm the patient without any interruption.

SUMMARY AND OBJECTS OF THE PRESENT INVENTION

The object of the present invention is to provide an irradiating device, which can be moved from an initial position to another position without any interruption in time and with extensively uniform irradiation of the lying surface in order to create space for additional examinations or manipulations on the patient.

According to the invention, a pivotable irradiating device is provided for irradiating a person on a lying surface (support surface). The irradiating device includes at least one radiator in a housing. The radiator produces a radiator beam with a central axis. The housing is connected to a securing element via a hinge, the axis of rotation of the hinge is located outside the central axis of the irradiating device. The intersection of these two axes (rotation and central axis) is located in the area of the center of the lying surface or in its vicinity, preferably above the plane of the lying surface.

The present invention provides an effective solution with a surprisingly simple design to a problem that was previously unsolved in this field of application. An essential advantage of the present invention is that by means of a hinge connection with a defined direction of the axis of rotation, the irradiating device can be pivoted from a starting position above the lying surface into at least one additional position, and the irradiation of the lying surface is continued extensively uniformly at the same time, so that the patient is kept continuously warm.

Since the irradiating device is no longer located vertically above the lying surface after it has been pivoted away, another effect is obtained: Even though the distance between the irradiating device and the center of the lying surface remains constant, the distance between the irradiating device and the outer areas of the lying surface does not. If the rays are assumed to exit from the irradiating device with an opening angle (divergently) rather than in parallel, the energy density decreases with increasing distance from the irradiating device. The areas of the lying surface facing the irradiating device therefore receive a higher radiation density than the areas facing away from it. To correct this disadvantage the axis of rotation of the hinge should preferably not point exactly toward the center of the lying surface, but toward a point that is somewhat above the center of the lying surface. A similarly uniform energy density distribution can be achieved on the lying surface with this correction as with the irradiating device not having been pivoted away.

The pivotable irradiating device is held according to the present invention by a securing element, which is in turn rigidly connected to the lying surface, a bracket carrying same, a frame or even an entire intensive care unit. As an alternative, it is possible for the irradiating device to be secured to a movable stand or a wall of the room via a hinge. In any case, it is important for the axis of rotation of the hinge to be located outside or spaced away from the central axis of the irradiation beam or irradiation flux and for the intersection of these two axes to be located in the center of the lying surface or in its vicinity.

The rotatable connector (hinge) preferably has a brake and/or a shock absorber (damper) to slow or dampen the movement of the rotatable connector. This allows for a controlled movement of the irradiating device.

The housing of the irradiating device contains, in general, a plurality of infrared radiators, which are arranged next to each other and irradiate and warm the lying surface and consequently the patient from the top and as uniformly as possible.

Additional light sources of a suitable number, power, and frequency may be located in the housing for the purpose of phototherapy and for illuminating the patient in the visible wavelength range for diagnostic purposes.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention are illustrated.

DESCRIPTION OF THE PREFERRED EMBODIMENT

Figure 1:
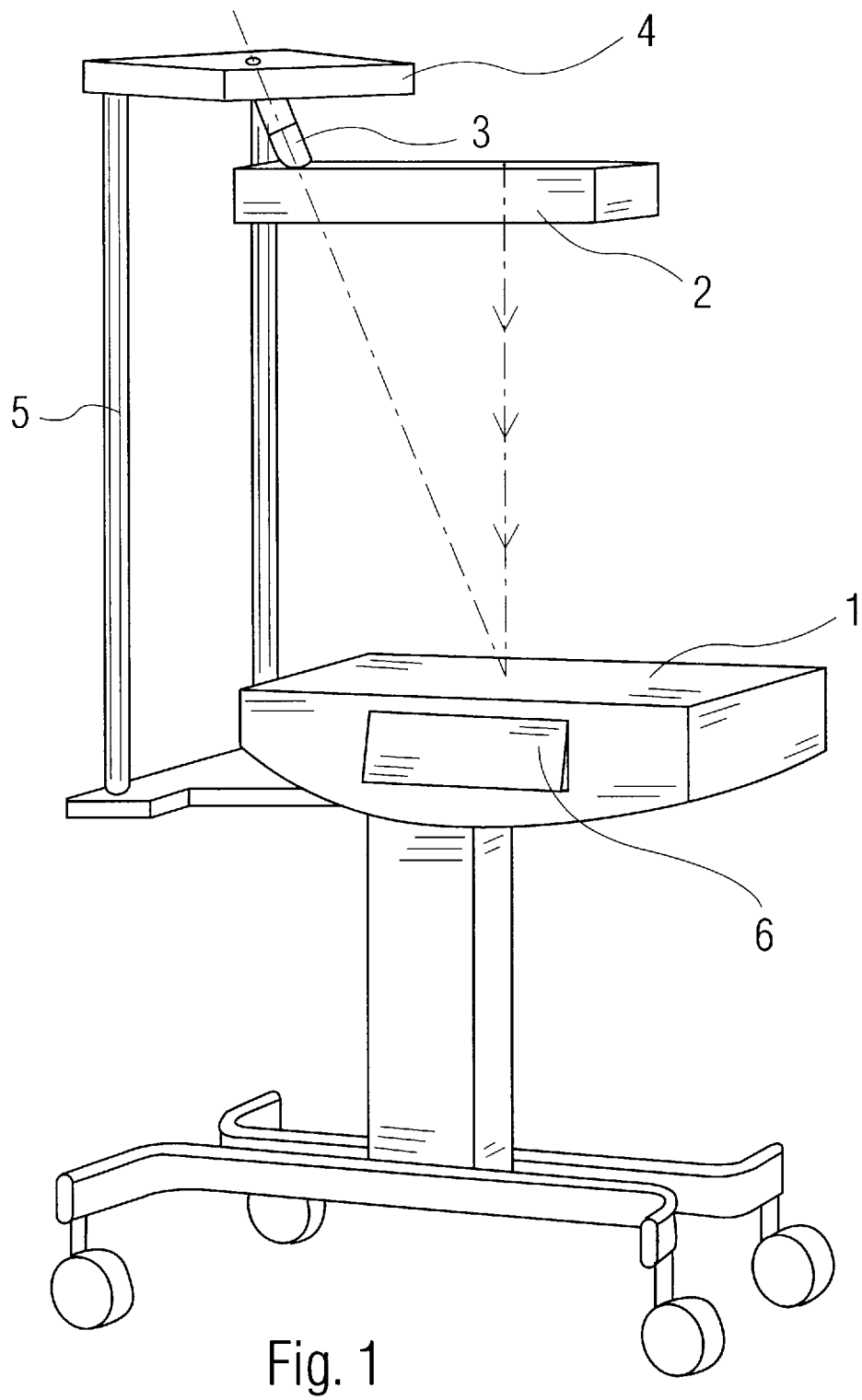
FIG. 1 is a perspective view of the irradiation device in its normal position.

Referring to the drawings in particular, the lying surface or support 1 with the patient lying thereon (not shown) is kept warm by heat radiation by means of radiators located above it in the housing 2. The radiators produce a radiation flux or radiation beams with a radiation central axis (normally corresponding to the line of maximum radiation intensity). This central axis of action of the heat radiation is set to a centrally located point of the lying surface 1, in this case to the geometric center, so that a pattern of symmetric lines of equal energy density of the heat radiation is obtained on the lying surface 1. FIG. 1 shows the normal starting position for the heat irradiation of the patient. The housing 2 is usually rigid or is pivotable only laterally around a vertical axis of rotation, so that the heat irradiation of the lying surface is completely or at least partially interrupted when the irradiating device is pivoted away, which is undesirable.

The housing 2 is connected according to the present invention to a securing element 4 via a hinge 3. In the schematic representation, the securing element 4 is directly connected, in the form of a frame 5, to the lying surface 1. The lying surface 1 is normally part of an open intensive care unit or of an opened incubator, in which case the frame 5 is designed in the form of, e.g., a tube or a stand.

It is important according to the present invention for the extension of the axis of rotation of the hinge 3 to reach the lying surface 1 in the center and for the central axis of the radiation flux also to reach the lying surface 1 through the center of the lying surface 1, while the axis of rotation of the hinge 3 and the central axis of the radiation flux do not extend in parallel to one another and meet in the center of the lying surface 1.

Figure 2:
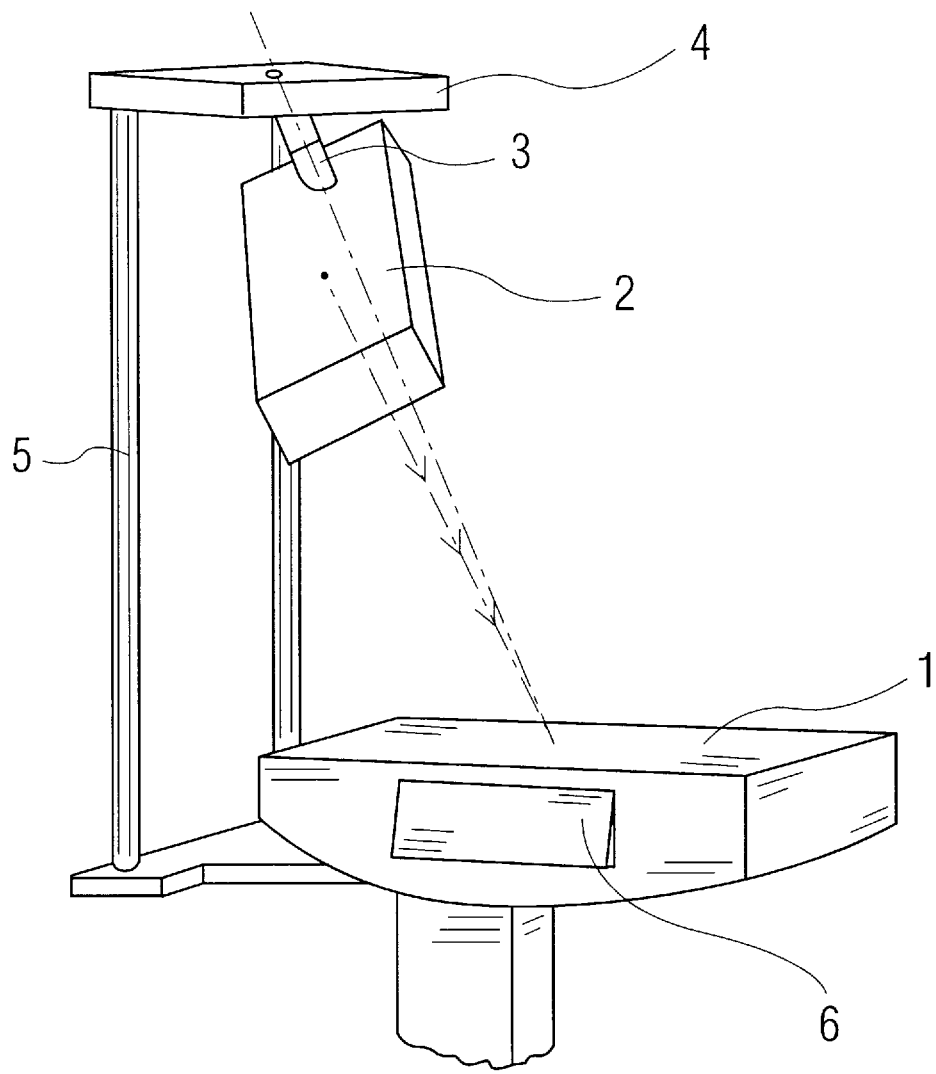
FIG. 2 is a perspective view, partially broken away of the irradiation device with the housing swung away into a pivoted position.
Figure 3:
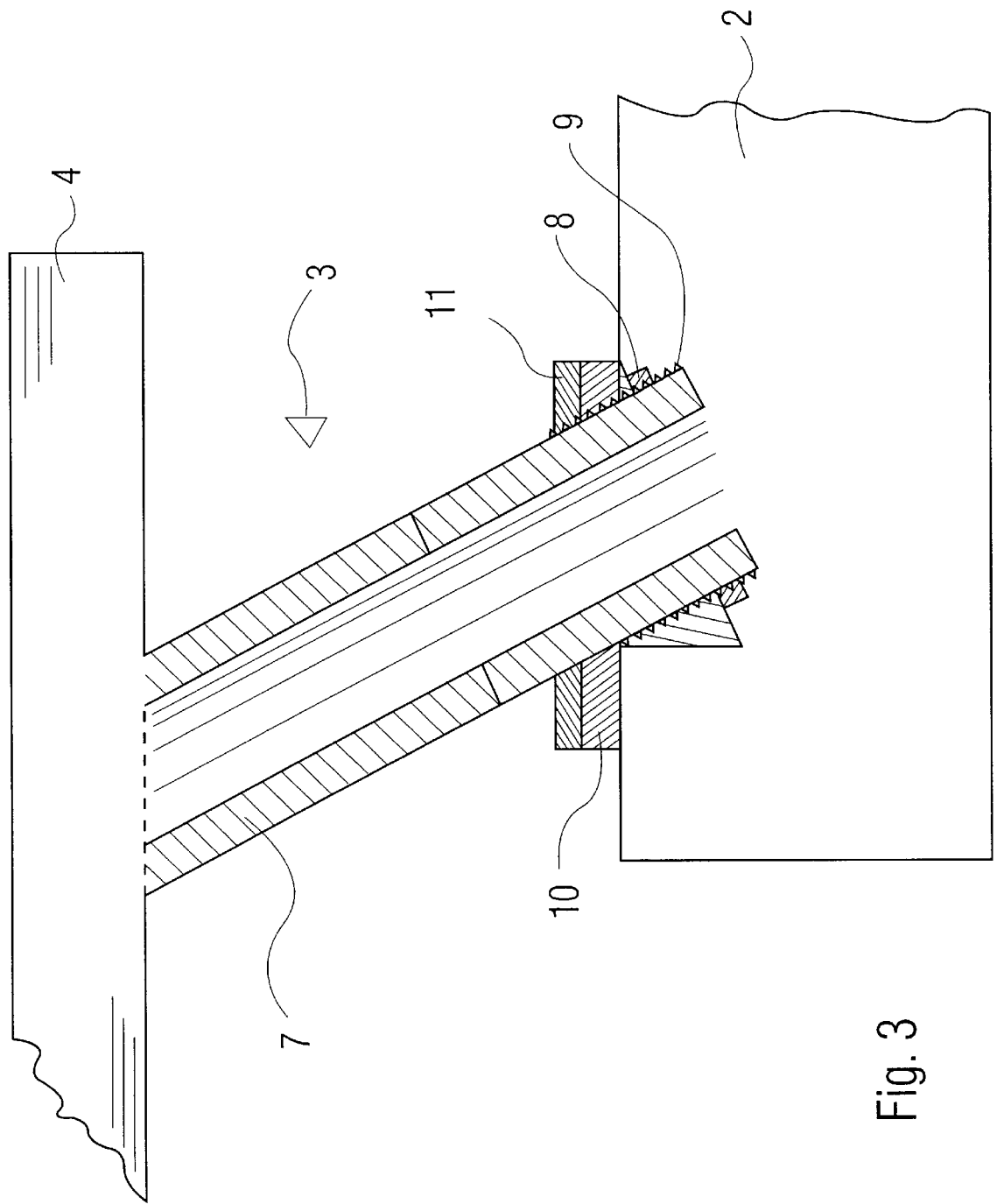
FIG. 3 is a cross sectional view of the connector.

When the housing 2 is pivoted away into the position shown in FIG. 2, e.g., by 90° in relation to the starting position, the following effects are produced. The housing 2 of the irradiating device frees the space above the lying surface 1 in order to use, e.g., an X-ray apparatus there. The housing 2 has been rotated in three planes, but the axis of action of the radiation continues to point toward the center of the lying surface 1. The distance between the housing 2 with the irradiating lamps and the center of the lying surface 1 has not changed. The energy density on the center of the lying surface 1 has changed only by the cosine of the changed angle of incidence of the rays on the lying surface 1. Further, the pattern of the lines of equal radiation energy density on the lying surface 1 has rotated by 90°.

The rotatable connector or hinge 3 is preferably constructed as a hollow shaft 7, so that the connection cables for the radiators and lamps in the housing 2 from the frame 4 and ultimately from a corresponding supply and control unit 6 can pass through the hollow shaft 7. An arrangement of a hollow nut 8 and a hollow screw 9 engaging each other has proved to be a structurally simple design of a hinge 3 based on a small number of parts. The fine-pitch thread is used as a pivot bearing. The normal position of the housing as well as defined pivoted positions can be secured with a locking means, brake, or stop 10 e.g., in the form of spring-loaded balls. A damper or shock absorber 11 can be used to slow movement of the housing. Besides for heat irradiation, the present invention can also be used for irradiation with electromagnetic waves of different wavelengths for diagnostic or therapeutic purposes.

While a specific embodiment of the invention has been shown and described in detail to illustrate the application of the principles of the invention, it will be understood that the invention may be embodied otherwise without departing from such principles.

What is claimed is:

1. A pivotable irradiating device for irradiating a person, comprising:

a housing supporting at least one radiator, said radiator for producing heat radiation having a central axis of action;

a securing element;

a lying surface connected to said securing element;

a rotatable connector having a connector axis located outside said central axis of action, said rotatable connector rotatably connecting said housing to said securing element, about said connector axis, said connector axis intersecting said central axis adjacent to or at a center of said lying surface, said connector axis extends axially through said connector.

2. A pivotable irradiating device in accordance with claim 1, wherein said point of intersection is above a plane of said lying surface.

3. A pivotable irradiating device in accordance with claim 1, wherein said housing is movable between an initial position, above and parallel to said lying surface and a pivoted position, pivoted about said axis of rotation relative to said initial position, said connector axis intersecting said central axis adjacent to or at a center of said lying surface in each of said initial position and said pivoted position.

4. A pivotable irradiating device in accordance with claim 1, wherein said rotatable connector includes a hollow portion containing connection cables for the radiators.

5. A pivotable irradiating device in accordance with claim 4, wherein said rotatable connector includes a hollow nut and hollow screw engaging each other.

6. A pivotable irradiating device in accordance with claim 1, wherein said rotatable connector includes at least one of a brake and a damper.

7. A pivotable irradiating device in accordance with claim 1, wherein said rotatable connector includes dampening means for dampening movement of said housing relative to said securing element.

8. A pivotable irradiating device in accordance with claim 7, wherein said dampening means includes a shock absorber type damper and a brake.

9. A pivotable irradiating device in accordance with claim 1 wherein said rotatable connector is provided with a stop means for a predefined positioning of the housing in one of different pivoted positions.

10. A pivotable irradiating device in accordance with claim 1, wherein said securing element is rigidly connected to the said lying surface.

11. A pivotable irradiating device in accordance with claim 1, wherein said securing element is fixed in a position in space in relation to said lying surface.

12. A device in accordance with claim 1, wherein:

said connector axis extends through a plane of said housing.

13. A pivotable irradiating device comprising:

a housing including at least one radiator means for producing heat radiation on a surface, said heat radiation having a central axis of action;

a frame;

a support for supporting an object to receive said heat radiation, said support being connected to said frame, said surface being located at one of on said support and adjacent said support;

a connector rotatably connecting said housing to said frame about a connector axis, said connector axis being angularly spaced from said central axis and intersecting said central axis at said surface, said connector axis extending axially through said connector.

14. A device in accordance with claim 13, wherein:

said surface is between said support and said housing.

15. A device in accordance with claim 13, wherein:

said connector axis is angularly spaced from said support.

16. A device in accordance with claim 13, wherein:

said radiator means varies said heat radiation on said surface as a cosine function of angular rotation of said housing about said connector axis.

17. A device in accordance with claim 13, wherein:

said intersecting of said central axis and said connector axis is at a center axis of said support.

18. A pivotable irradiating device comprising:

- a housing including at least one radiator means for producing heat radiation on a surface, said heat radiation having a central axis of action;
- a frame;
- a support for supporting an object to receive said heat radiation, said support being connected to said frame, said surface being located at one of on said support and adjacent said support;
- a connector rotatably connecting said housing to said frame about a connector axis, said connector axis being angularly spaced from said central axis and intersecting said central axis at said surface, said connector axis extends axially through said housing.

* * * * *